United States Patent [19]

Fujita et al.

[11] Patent Number: 5,206,615
[45] Date of Patent: Apr. 27, 1993

[54] SENSOR FOR MEASURING SOLUTE CONCENTRATION IN AN AQUEOUS SOLUTION

[75] Inventors: Yuko Fujita; Hisashi Kudo; Yoshiharu Iwanami, all of Kyoto; Haruo Nomi; Yoshihiko Shibata, both of Okayama; Ryozo Ueno, Tokyo, all of Japan

[73] Assignee: W. L. Gore & Associates, Inc., Newark, Del.

[21] Appl. No.: 582,212

[22] PCT Filed: Mar. 31, 1989

[86] PCT No.: PCT/JP89/00350
§ 371 Date: Sep. 19, 1991
§ 102(e) Date: Sep. 19, 1991

[87] PCT Pub. No.: WO89/09387
PCT Pub. Date: Oct. 5, 1989

[30] Foreign Application Priority Data

Mar. 31, 1988 [JP] Japan .................................. 63-76210

[51] Int. Cl.$^5$ ............................................. H01C 7/00
[52] U.S. Cl. ................................. 335/35; 73/29.02; 73/335; 73/29.03; 73/64.45
[58] Field of Search ............... 338/35; 73/29.05, 29.01, 73/29.02, 335; 428/411.1

[56] References Cited

U.S. PATENT DOCUMENTS

| 4,263,576 | 4/1981 | Murata et al. | 338/35 |
| 4,656,455 | 4/1987 | Tanino et al. | 338/35 |

FOREIGN PATENT DOCUMENTS

| 2254207 | 11/1973 | Fed. Rep. of Germany . |
| 2597978 | 4/1986 | France . |
| 54-139097 | 4/1979 | Japan . |
| 55-29774 | 11/1980 | Japan . |
| 57-147034 | 8/1982 | Japan . |
| 58-169049 | 10/1983 | Japan . |
| 62-3366 | 1/1987 | Japan . |

OTHER PUBLICATIONS

Journal of the Electrochemical Society, vol. 129, No. 11 pp. 2409-2412.

Primary Examiner—Marvin M. Lateef
Attorney, Agent, or Firm—Gary A. Samuels

[57] ABSTRACT

A sensor for measuring concentrate of solute in an aqueous solution in which a humidity sensor is enclosed and sealed within a porous fluorine polymer film that is liquid water impermeable but water vapor permeable. The sensor operates by measuring water vapor pressure in the gaseous phase inside the sealed film after the inside and outside have equilibrated with respect to water outside and inside.

4 Claims, 5 Drawing Sheets

1 HUMIDITY SENSOR
2 POROUS NON-WATER PERMEABLE FLUORINE RESIN FILM

SENSOR FOR MEASURING SOLUTE CONCENTRATION IN AN AQUEOUS SOLUTION

FIELD OF THE INVENTION

The present invention relates to a sensor for measuring solute concentration in an aqueous solution and more particularly, provides a sensor which is suitable for simple and continuous detection and measurement of the concentration of the solute in an aqueous solution from the water vapor pressure of the solution.

BACKGROUND OF THE INVENTION

As a means for measuring a solute concentration in an aqueous solution, chemical analysis, or instrumental analysis such as atomic absorption spectroscopy, ion chromatography, etc. has been adopted heretofore.

Further as a simpler means, a hydrometer, an optical refraction type gravimeter, a conductivity meter, etc. may be used.

There are many demands on simple measurement of aqueous solutions of acids such as sulfuric acid, hydrochloric acid, acetic acid, etc. but the measurement is extremely difficult. For example, a concentration of sulfuric acid which is an electrolyte of a lead-acid battery is in a close relationship to a charge and discharge state of the lead-acid battery and therefore, it has been strongly desired to develop a simple method for measuring a sulfuric acid concentration. However, such an adequate measurement technique has not been attained yet. And it is general to determine the concentration with a hydrometer, an optical refraction type gravimeter, etc. described above. As a particular method, it is proposed in West German Patent No. 2,254,207 (1973) to determine a sulfuric acid concentration by measuring a water vapor pressure of the upper space beyond a sulfuric acid electrolyte of a lead-acid battery. That is, this method comprises measuring a water vapor pressure in the upper space in a gas-liquid equilibrated state with a sulfuric acid aqueous solution to determine a concentration of the sulfuric acid aqueous solution since the water vapor pressure of the space varies depending upon the sulfuric acid concentration. This proposal has further been advanced and it has been proposed in J. L. Weininger, J. L. Briant., J. Electrochem. Soc., VOL 129, 2409 (1982) to cover a humidity sensor with a porous polypropylene film, directly immersing the covered humidity sensor in a sulfuric acid aqueous solution and measure partial pressure of water vapor diffused through pores of the porous polypropylene film.

Conventional chemical analysis and instrumental analysis described above generally require equipment in a large scale and at the same time, operations are complicated. Even the operation with a hydrometer, an optical refraction type gravimeter and a conductivity meter are complicated and skill is required for measurement. Besides, it is generally inadequate for continuously monitoring a change in concentration of an aqueous solution.

Upon measurement of a concentration of an aqueous solution of acids such as sulfuric acid, etc. described above, in particular, sulfuric acid as an electrolyte in a lead-acid battery, a hydrometer or an optical refraction type gravimeter has an excessively large size so that the meter cannot be inserted into the lead-acid battery, which makes continuous measurement impossible.

According to the method of West German patent supra, when a sulfuric acid concentration changes, it takes a long time until the water vapor pressure of the sulfuric acid aqueous solution and the water vapor pressure of the space reach equilibrium and a response speed is slow. Further, according to the method of Weininger, et al, the porous polypropylene film has a problem in its material, that is, owing to insufficient water repellency, not only water vapor but also the sulfuric acid aqueous solution itself permeate through the film to reach a moisture-sensitive part of the humidity sensor so that it is difficult to properly determine a humidity. In addition, the life of a sensor is extremely short because of chemical corrosion by sulfuric acid.

SUMMARY OF THE INVENTION

A sensor for measuring a concentration of a solute in an aqueous solution, characterized in that a humidity sensor is covered with a porous liquid water impermeable water vapor permeable fluorine polymer film having a moisture vapor transmission rate (hereinafter MVTR) of from 500 to 150000 $g/m^2$ per 24 hr.

A sensor for measuring a concentration of a solute in an aqueous solution, characterized in that a humidity sensor is covered with a porous liquid water impermeable water-vapor fluorine polymer film having an MVTR of from 500 to 150000 $g/m^2$ per 24 hr, said fluorine polymer film having a selective water vapor-permeable layer associated therewith.

A sensor for measuring a concentration of a solute in an aqueous solution, characterized in that a humidity sensor is covered with a porous liquid water impermeable water vapor permeable fluorine polymer film having MVTR of from 500 to 150000 $g/m^2$ per 24 hrs, said fluorine polymer film having both a selective water vapor-permeable layer and an acid vapor-absorbing layer associated therewith.

BRIEF DESCRIPTION OF THE DRAWINGS

The figures indicate technical contents of the present invention.

In these figures, numeral 1 shows a humidity sensor, 2 denotes A porous non-water-permeable fluorine polymer film, 3 denotes a selective water vapor-permeable layer, and 4 denotes an acid vapor-absorbing layer.

DESCRIPTION OF THE INVENTION

When the humidity sensor is covered with a porous liquid water impermeable, water vapor permeable fluorine polymer film having MVTR of from 500 to 150000 g/m$^2$ per 24 hrs, preferably 500 to 10000 g/m$^2$ per 24 hrs and immersed into an aqueous solution, water in the aqueous solution permeates through the polymer films in the form of vapor, and liquid and vapor are equilibrated on both sides of the film, whereby a water vapor pressure in the gaseous phase inside of the film is detected as humidity by the humidity sensor. Accordingly, by previously measuring the relationship between a solute concentration and a water vapor pressure of an aqueous solution to be measured or by previously determining the relationship between a known concentration of the solute and a relative humidity value of the humidity sensor, a solute concentration of the aqueous solution can be determined by a relative humidity value when the humidity sensor for measuring the solute concentration of the aqueous solution covered with the porous fluorine resin film is immersed in an aqueous solution having an unknown concentration to be measured.

Figure 1:
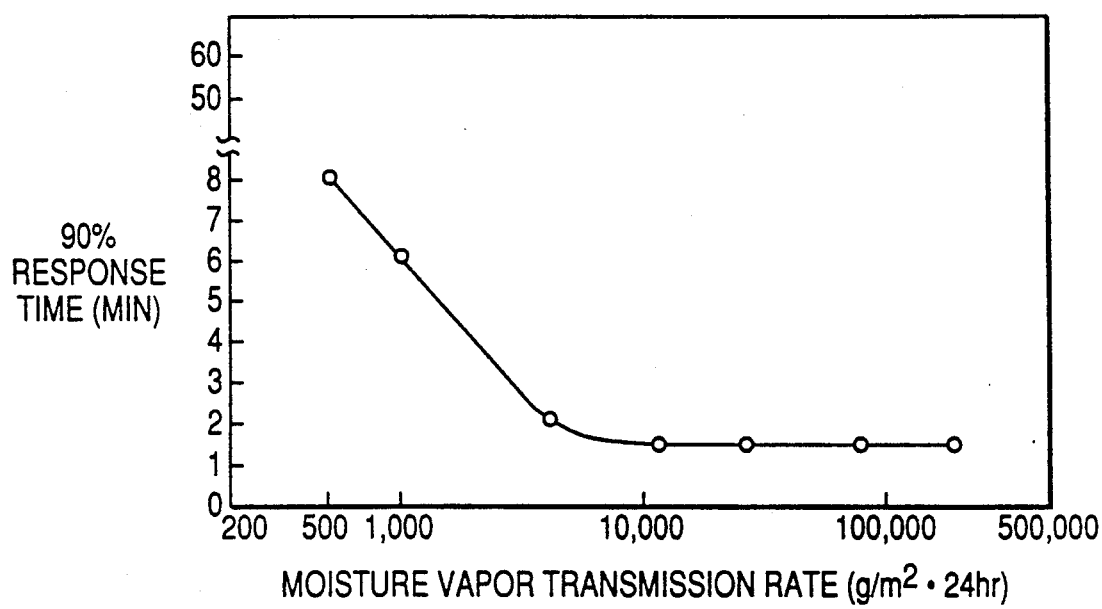
FIG. 1 shows a relationship between a moisture vapor transmission rate of covered film of the humidity sensor adopted in the present invention and a sensor response time.

The porous fluorine polymer film described above should provide a high response speed of the sensor for the aqueous solution concentration. For this purpose, the polymer film should be as water vapor permeable and porous as possible and have a thickness as thin as possible. On the other hand, in view of the mechanical strength and life of the sensor, the polymer film should be less porous and thicker. To satisfy such contradictory requirements, the present inventors have found that the moisture vapor transmission rate (measured by Japanese Industrial Standards L-1099) of the polymer film is an important factor for determining response speed and life of the aqueous solution concentration sensor and have determined a relationship between such a moisture vapor transmission rate of the film. The relationship between the moisture vapor transmission rate and the response time of the sensor is depicted in FIG. 1. That is, in case that the moisture vapor transmission rate is less than 500 g/m$^2$ per 24 hrs, the aqueous solution concentration sensor exhibits too low a response speed and is not generally applicable to measure a change in concentration of the aqueous solution. Further, in the case that the moisture vapor transmission rate is larger than 150000 g/m$^2$ per 24 hrs, not only water vapor but also liquid water permeate through the film to cause an error in the humidity sensor, or, depending upon the kind of solute, the solute might permeate through the film to corrode the humidity sensor. It is thus mandatory to set the upper limit at 150000 g/m$^2$ per 24 hrs.

Covering the humidity sensor with a double-layered film obtained by additionally coating or laminating the porous fluorine polymer film described above with a selective water vapor-permeable layer such as perfluorocarbon sulfonic acid makes more accurate measurement possible, since water vapor alone permeates and solute vapor does not permeate. This double-layered film shows effectiveness especially in an aqueous solution of a solute having high vapor pressure. Moreover, life of the humidity sensor is prolonged.

Further by forming an acid vapor-absorbing layer using calcium carbonate, for example, together with the selective water vapor-permeable layer described above, a trace amount of acidic vapor that cannot be intercepted by the selective water vapor-permeable layer can be trapped. That is, this trapping is effected by chemical reaction as:

$$H_2SO_4 + CaCO_3 \rightarrow CaSO_4 + CO_2 + H_2O$$

The acid vapor-absorbing layer described above can easily be formed by coating a mixture of finely divided calcium carbonate and a binder such as fluorine-contained urethane resin or fluorine resin, etc.

EXAMPLES

Figure 2:
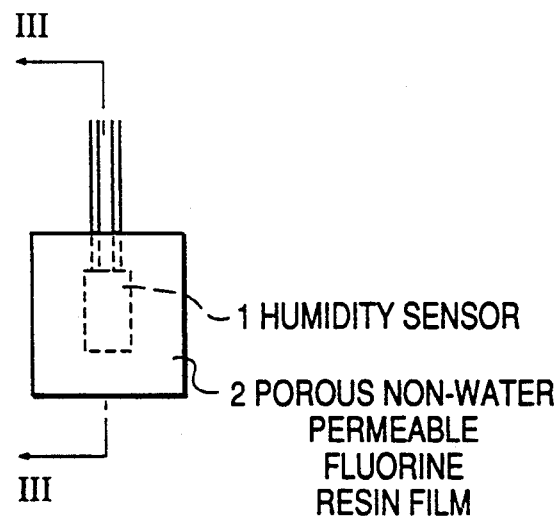
FIG. 2 is a front view of the sensor having the basic structure of the present invention.
Figure 3:
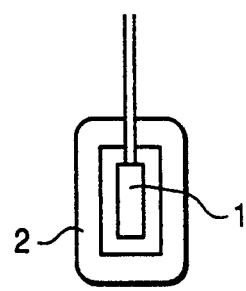
FIG. 3 is a cross sectional view of the sensor of FIG. 2.

Specific embodiments of the present invention are explained by referring to the figures appended. Basic embodiments of the present invention are as shown in FIGS. 2 and 3. For example, a concentration detector element 1 composed of a commercially available polymer type humidity sensor or ceramic type humidity sensor is covered and is heat-sealed with a porous liquid water impermeable water vapor permeable fluorine polymer film having a moisture vapor transmission rate of from 500 to 150000 g/m$^2$ per 24 hrs. That is, the fluorine polymer described above has a water repellency showing an advanced contact angle of about 110. This film is made by roll-pressing and stretching and having the maximum pore diameter of 0.5 μm, preferably 0.01 to 0.2 μm and porosity of 25 to 85%, preferably 50 to 80%. Thus, the film is obtained as having an appropriate liquid-water-impermeable property while it has a preferred moisture vapor transmission rate. In addition, the film has excellent resistivity to acid and other chemicals.

Figure 4:
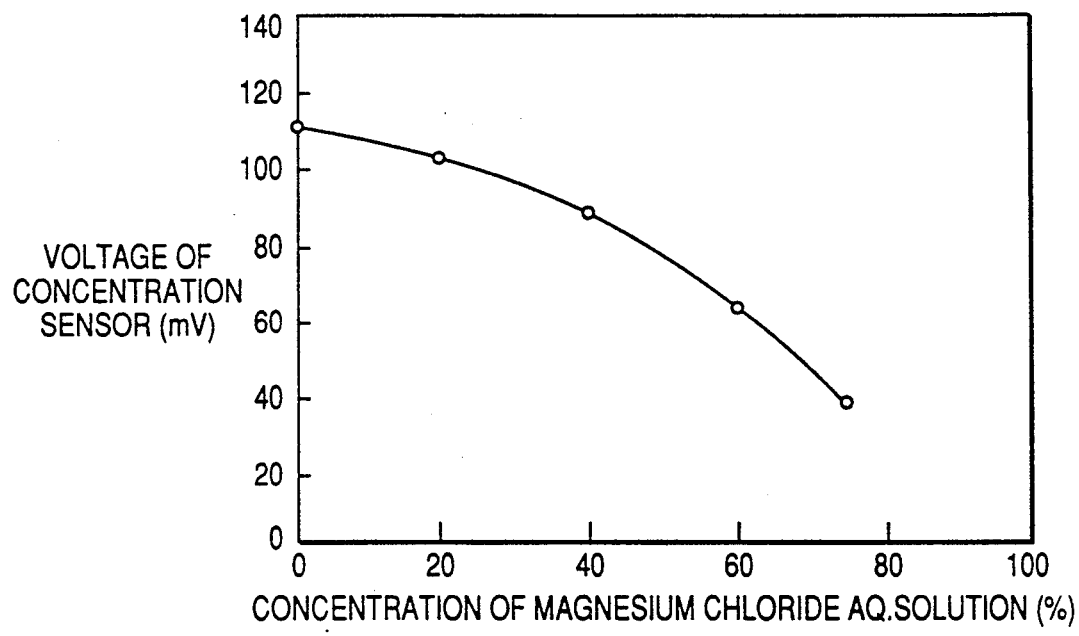
FIG. 4 shows a relationship between a concentration of aqueous magnesium chloride solution and a value obtained by an aqueous solution concentration sensor.

As a specific embodiment, the aqueous solution concentration sensor was prepared by using the concentration detection element 1 consisting of the polymer type humidity sensor whose out-put signal was designed by electric circuit to express a relative humidity by voltage, covering the humidity sensor with a porous polytetrafluoroethylene film 2 having a maximum pore diameter of 0.5 μm and porosity of 75% and having a thickness of 0.1 mm, and heat sealing the covering. The sensor was immersed in aqueous solutions of magnesium chloride hexahydrate (MgCl$_2$.6H$_2$O) adjusted to various concentrations and output voltages by the aqueous solution concentration sensor were measured. The results are shown in FIG. 4.

That is, as the concentration of magnesium chloride aqueous solution becomes high, the voltage of the aqueous solution concentration sensor becomes low. It is thus clear that the concentration of magnesium chloride can be accurately detected by the voltage value measured. Further in this case, a response rate of the aqueous solution concentration sensor was determined based on the change in voltage when a concentration of the magnesium chloride aqueous solution was changed, whereby 90% response took 3 minutes which was a considerably rapid response and it was confirmed that the measurment could be sufficiently practically usable.

In addition, the concentration of magnesium chloride was continuously measured using this aqueous solution concentration sensor, while changing the concentration of magnesium chloride. The detection characteristic as described above did not change even after 1000 hours passed. It was confirmed that the sensor showed a satisfactory long life and the method exhibited excellent reproductivity.

Figure 5:
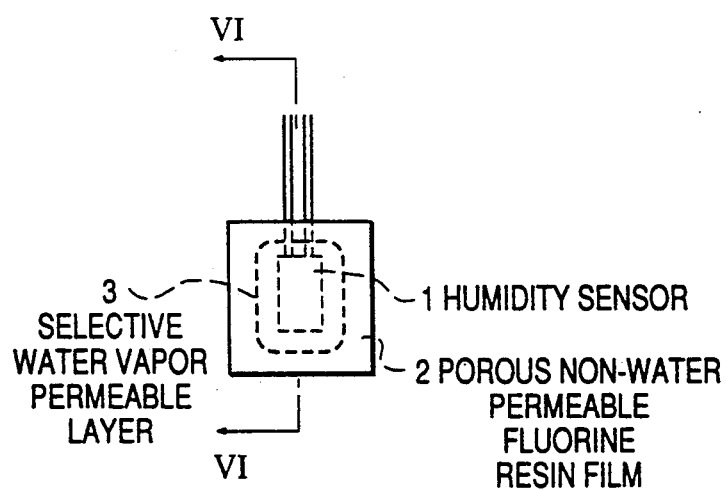
FIG. 5 is a front view of the second embodiment of the present invention as shown in FIG. 2
Figure 6:
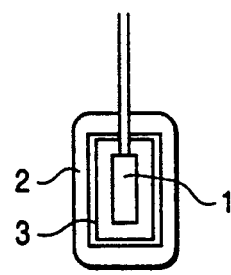
FIG. 6 is its cross-sectional view.

A second embodiment of the present invention is shown in FIGS. 5 and 6. A double-layered plastic film was obtained by coating an alcohol solution of perfluorocarbon sulfonic acid on one surface of the same porous non-water-permeable film as in FIGS. 2 and 3 to form a selective water vapor-permeable layer 3. Then humidity sensor 1 was covered and heat-sealed with the plastic film at its periphery as in FIGS. 5 and 6.

Figure 7:
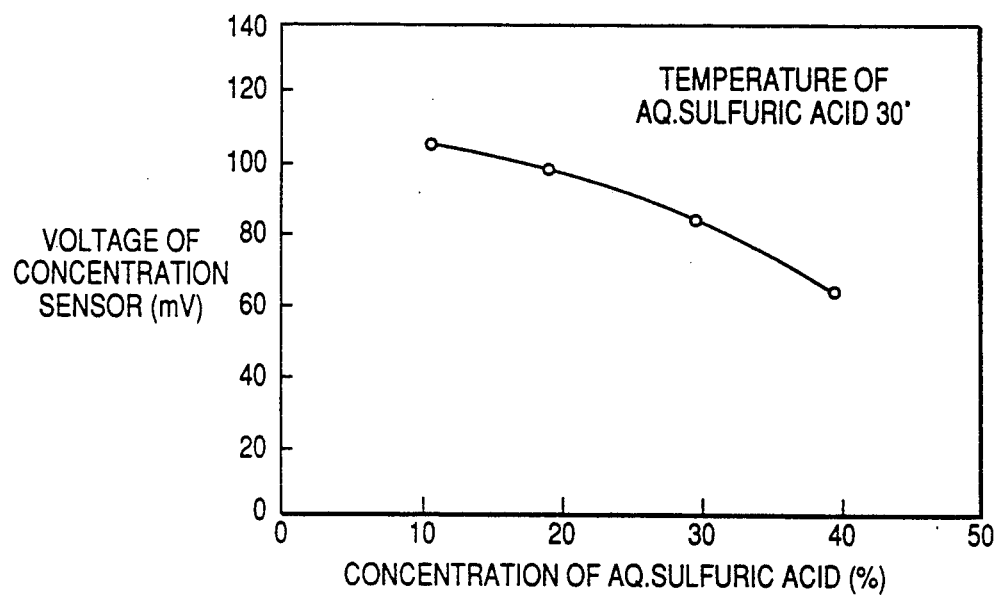
FIG. 7 shows a relationship between a concentration of sulfuric acid aqueous solution and a voltage detected by the aqueous solution concentration sensor.

The sensor was immersed in aqueous solutions of sulfuric acid adjusted to various concentrations and output voltages were measured. The results are shown in FIG. 7. It was confirmed that preferable measurement was possible as in FIG. 4. Further, a response rate was determined as in FIGS. 2 and 3. Rapid response shown as 90% response for 3 minutes, was obtained and it was confirmed that the measurement was sufficient for practical use.

Figure 8:
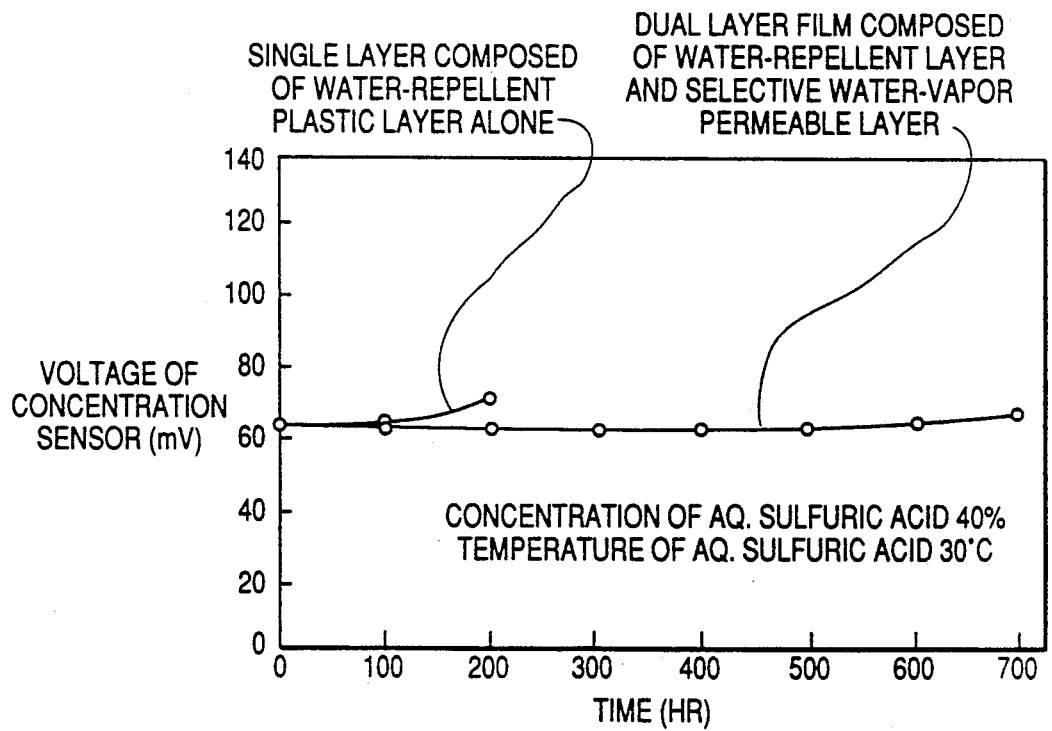
FIG. 8 shows a change with voltage depending on time under constant concentration conditions of the sulfuric acid aqueous solution.

In addition, when the concentration of sulfuric acid was continuously measured using this aqueous solution concentration sensor, change in the sensor characteristics was continuously monitored. The results are shown in FIG. 8, together with those of the sensor shown in FIGS. 2 and 3 having no selective water vapor-permeable layer 3. The sensors showed a preferable long life under the severe condition of 40% sulfuric acid and temperature of 30° C. In particular, with the sensor of FIGS. 5 and 6, no abnormality was noted in characteristics even after 500 hours passed. It was confirmed that the measurement method showed excellent reproductivity.

Figure 9:
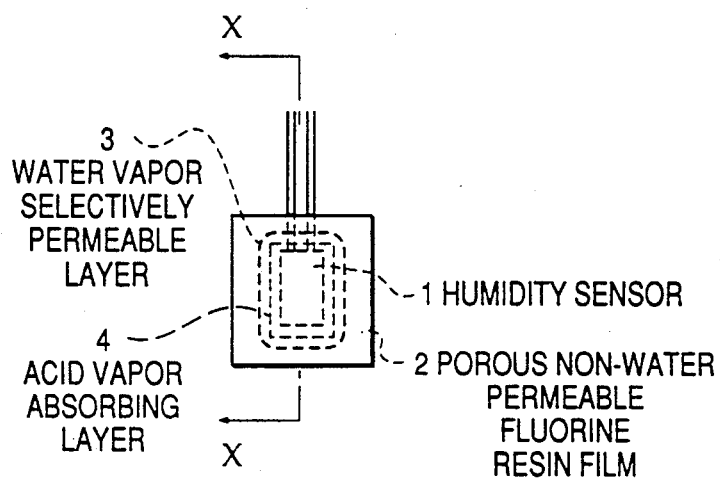
FIG. 9 is a front view of the third embodiment of the present invention as shown in FIG. 2 and FIG. 5.
Figure 10:
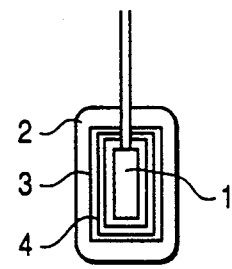
FIG. 10 is its cross sectional view.

A third embodiment of the present invention is shown in FIGS. 9 and 10. A sensor was prepared by further forming an acid vapor-absorbing layer 4 obtained by binding calcium carbonate with a binder onto a water vapor selectively permeable layer 3 formed on a porous non-water-permeable layer 2.

Figure 11:
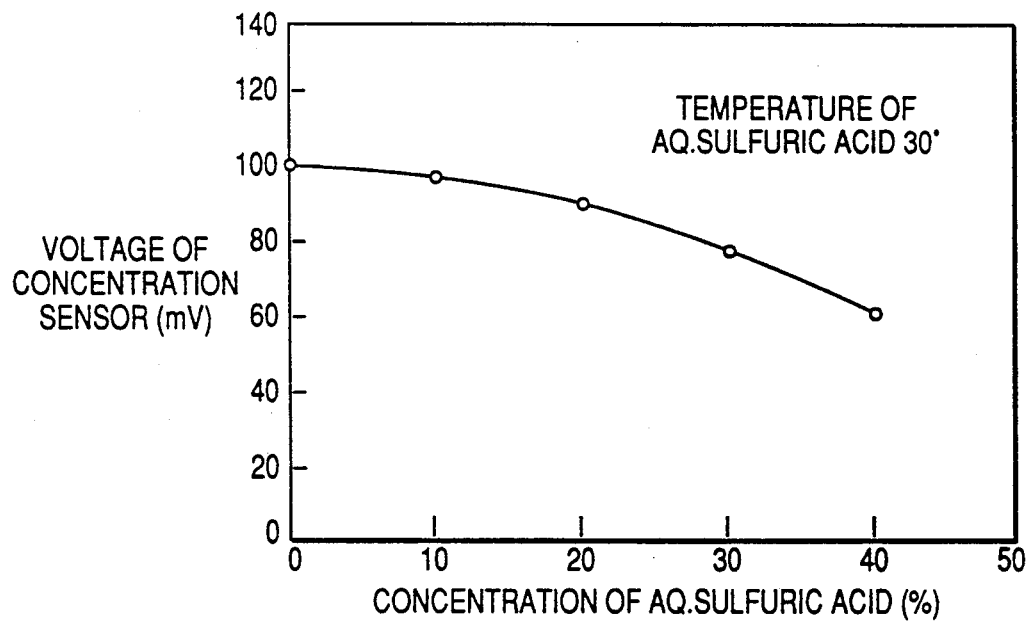
FIG. 11 shows a relationship between a concentration of aqueous sulfuric acid solution and a voltage detected by the aqueous solution concentration sensor.

More specifically, a mixture of calcium carbonate powders having a particle diameter of 20 μm or less and fluorine-modified urethane resin was used to form an acid vapor-absorbing layer 4. This sensor was immersed in aqueous solutions of sulfuric acid adjusted to various concentrations and the relationship between the concentrations of the solutions and output voltages of the sensor was examined. The results are shown in FIG. 11. It is clear that the concentration of the sulfuric acid aqueous solution can be adequately determined by voltages measured. Considerably rapid response shown as 90% response for 3 minutes, was obtained and it was confirmed that the response was sufficient for practical use.

Figure 12:
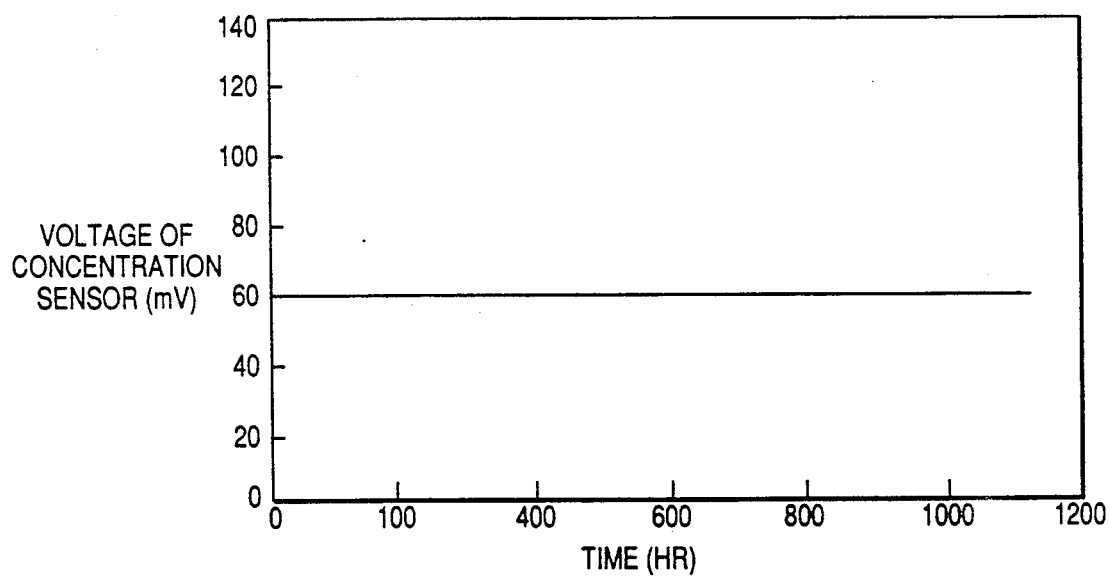
FIG. 12 shows a change of voltage depending on time under constant concentration conditions of the sulfuric acid aqueous solution.

In addition, when the concentration of sulfuric acid was continuously measured using this aqueous solution concentration sensor, change in the sensor characteristics was continuously monitored. That is, the sulfuric acid aqueous solution having a concentration of 40% was measured over 1100 hours at a temperature of 30° C. The results are shown in FIG. 12. A measured voltage of the aqueous solution concentration sensor indicates continuously the stable value of 60 mV. It was confirmed that continuous and accurate detection measurement could be made on a sulfuric acid concentration in a lead-acid battery over a sufficiently long period of time.

It is apparent that embodiments other than the humidity sensors described above and almost similar results can be obtained.

We claim:
1. A sensor for measuring a concentration of a solute in an aqueous solution, characterized in that a humidity sensor is surrounded by and sealed within a porous liquid water impermeable water vapor permeable fluorine polymer film having a moisture vapor transmission rate of from 500 to 150000 g/m$^2$ per 24 hrs.

2. The sensor of claim 1 characterized in that said fluorine polymer film has a selective water vapor-permeable material attached thereto.

3. The sensor of claim 2 characterized in that said selective water vapor-permeable material has an acid vapor-absorbing layer attached thereto.

4. The sensor of claim 1, 2 or 3 wherein the fluorine polymer film is porous polytetrafluoroethylene.

* * * * *